United States Patent [19]

Bair

[11] Patent Number: 5,744,463
[45] Date of Patent: Apr. 28, 1998

[54] TREATMENT OF SIDE EFFECTS OF PROGESTINS AND PROGESTERONE ANALOGUES USED FOR BIRTH CONTROL

[76] Inventor: Glenn O. Bair, 5520 SW. Lincolnshire Cir., Topeka, Kans. 66614

[21] Appl. No.: 656,737

[22] Filed: Jun. 3, 1996

[51] Int. Cl.[6] ............................................ A61K 31/56
[52] U.S. Cl. ........................ 514/177; 514/170; 514/922
[58] Field of Search ................................. 514/170, 177, 514/922

[56] References Cited

U.S. PATENT DOCUMENTS

| 4,900,734 | 2/1990 | Maxson et al. | 514/171 |
| 5,565,199 | 10/1996 | Page et al. | 424/195.1 |

*Primary Examiner*—Kimberly Jordan
*Attorney, Agent, or Firm*—Fish & Neave; Andrew S. Marks

[57] ABSTRACT

The present invention provides methods for treating the deleterious effects of progestins and progesterone analogues used for birth control. The invention also provides pharmaceutical compositions useful in those methods.

10 Claims, No Drawings

TREATMENT OF SIDE EFFECTS OF PROGESTINS AND PROGESTERONE ANALOGUES USED FOR BIRTH CONTROL

TECHNICAL FIELD OF THE INVENTION

The present invention provides methods for treating the deleterious effects of progestins and progesterone analogues used for birth control. The invention also provides pharmaceutical compositions useful in those methods.

BACKGROUND OF THE INVENTION

The undesirable side effects commonly associated with the use of progesterone analogue-based contraceptive drugs are well documented [Facts and Comparison, pp. 104–8 (1996)]. They include headache, mood changes, nervousness, abdominal cramps, dizziness, weakness or fatigue, nausea, vaginal irritation, breast swelling and tenderness, bloating, swelling of the hands or feet, backache, depression, mastalgia, insomnia, acne rashes, hot flashes and joint pains and vomiting. These side effects are observed in a subpopulation of women using such contraceptive drugs.

The use of progesterone analogue-based contraceptive drugs has also been causally implicated in more serious disorders such as deep vein thrombosis, pulmonary embolus, breast cancer, cervical cancer, pseudotumor cerebri and stroke [D. K. Wysowski, L. Green, Obstet. Gynecol., 85(4), pp. 538–42 (1995)].

Recently, a new generation of long-acting progesterone analogue-based contraceptives have replaced short-acting oral contraceptive pills as a convenient method of preventing unwanted pregnancies. For example, medroxyprogesterone acetate (DepoProvera™) injected intramuscularly as a sterile suspension can prevent pregnancy for a period of up to three months. Another long acting contraceptive is levonorgestrel, a synthetic progestin (Norplant™). Norplant is subdermally implanted in silicone tubes. The subdermal implant releases a continuous dose of levonorgestrel for a period of up to five years. Removal of the implant ends the contraceptive effect, thus providing a convenient and reversible method of contraception.

Unfortunately, these long-acting progesterone analogues also cause undesirable side effects in a subpopulation of women. The most common side effects include nervousness, rash, headache, acne, skin or hair problems, weight changes, mood swings and abdominal pain. The use of levonorgestrel has also been implicated in a few serious cases of hypertension, stroke, thrombocytopenia, pseudotumor cerebri [D. K. Wysowski, L. Green, Obstet. Gynecol., 85(4), pp. 538–42 (1995)].

Alleviation of these side effects has typically involved the cessation of contraception, i.e., removal of the subdermal implant or halting the injections, etc. In some cases, however, the side effects are so severe that cessation of the contraception does not alleviate the acute symptoms.

It is thus an object of the present invention to provide a method of treating the deleterious side effects commonly associated with using progestins or progesterone analogues for birth control, especially those side effects that linger after contraception has been halted.

It is a further object of the present invention to provide pharmaceutical formulations suitable for treating the side effects commonly associated with using progestins or progesterone analogues for birth control.

SUMMARY OF THE INVENTION

The present invention provides methods for alleviating the undesirable side effects associated with the use of progestins for birth control. These methods comprise the step of administering to the patient a high dosage of natural progesterone in a pharmaceutically acceptable composition.

The present invention also provides pharmaceutical formulations for use in these methods.

DETAILED DESCRIPTION OF THE INVENTION

The present invention derives its efficacy from the hitherto unrecognized link between the side effects commonly associated with the use of progestins or progesterone analogues for birth control and the incidence of pre-menstrual syndrome in women suffering from those side effects.

The most common side effects associated with the use of progestins or progesterone analogues include headache, mood changes, nervousness, abdominal cramps, dizziness, weakness or fatigue, nausea, vaginal irritation, breast swelling and tenderness, bloating, swelling of the hands or feet, backache, depression, mastalgia, insomnia, acne rashes, hot flashes and joint pains and vomiting. These maladies occur in a subpopulation of women who take these contraceptives. Without being bound by theory, applicant believes that the undesirable side effects arise because the affected subpopulation of women also suffer from PMS. In such women, progestins amplify the PMS condition, thus causing the above-described side effects. This link between PMS and side effects of progestin contraceptives has not been previously recognized.

Applicant believes that women who suffer from PMS possess a genetic mutation in the transcription control region of one or more of the genes necessary for fat metabolism. This defect causes the symptoms associated with PMS. Specifically, applicant believes that this mutation is in a progesterone-responsive enhancer element—a portion of a gene capable of altering transcription levels through the binding of progesterone. This would explain the alleviation of PMS symptoms in patients treated with progesterone. The excess progesterone compensates for the lowered affinity of the mutated enhancer element for progesterone, and thus restores normal fat metabolism.

The use of progestins or progesterone analogues for birth control is based on the ability of the progestin to suppress the onset of the ovulation cycle. However, it is well known that these progestins are competitive inhibitors for progesterone receptor sites. For example, levonorgestrel, a long acting progestin administered subdermally, has 43% greater affinity for progesterone receptor sites than natural progesterone [W. Kuhnz et al., Contraception, 51(2), pp. 131–39 (1995)]. Applicant believes that this greater affinity of progestins for progesterone receptor sites competitively inhibits the ability of progesterone to bind to those sites.

In women who do not suffer from PMS, the progesterone produced by the body is sufficient to overcome this competitive inhibition and therefore maintain normal fat metabolism. Such women do not exhibit the side effects associated with the use of progestins for birth control.

On the other hand, the use of progestins in women who suffer from PMS worsens the already present deficiency in fat metabolism. The progestin competitively inhibits progesterone binding to enhancer elements. Thus, upon using progestins for birth control, a woman suffering from PMS will consequently exhibit abnormally severe PMS symptoms. This explains the inability of PMS patients to tolerate progestins or progesterone analogues used for birth control.

Thus, one aspect of the invention provides a method of treating the undesirable side effects commonly associated with the use of progestins or progesterone analogues for birth control. This method comprises the step of administering a pharmaceutical composition comprising a high dosage amount of progesterone effective in alleviating the symptoms observed in the patient and a pharmaceutically acceptable carrier.

The term "undesirable side effects", as used herein, means any or all of the symptoms associated with progesterone analogue-based contraceptives. These include headache, mood changes, nervousness, abdominal cramps, dizziness, weakness or fatigue, nausea, vaginal irritation, breast swelling and tenderness, bloating, swelling of the hands or feet, backache, depression, mastalgia, insomnia, acne rashes, hot flashes, angry outbursts, acute weight gain/loss, pain and swelling of the joints, hypertension, stroke, and vomiting.

The progestin or progesterone analogue whose side effects may be alleviated by the method of this invention can be any synthetic progesterone known to have a contraceptive effect in women. The common progestins used for birth control include norethindrone, norethindrone acetate, ethynodiol diacetate, norgestrel, desogestrel, levonorgestrel, medroxyprogesterone acetate. Preferably, the methods of this invention are used to alleviate the side effects of long acting progesterone analogues, such as levonorgestrel and medroxyprogesterone acetate.

According to the methods of this invention, a pharmaceutical composition comprising natural progesterone is administered to a patient in an amount effective to deliver a daily dosage of natural progesterone ranging from 1 g/day to 20 g/day. More preferably, the amount of progesterone delivered to the patient is between about 2 g/day to 10 g/day. Most preferably, the amount of progesterone delivered to the patient is between about 6 g/day to 9 g/day. The duration of the treatment depends on the severity of the undesirable side effects.

In addition to natural progesterone, the pharmaceutical compositions of the present invention also contain a pharmaceutically acceptable carrier. The choice of the carrier depends on the route of administration chosen. The progesterone compositions used in the present invention may be administered orally, intravenously, topically, parenterally, by inhalation spray, rectally, nasally, buccally or vaginally. Preferably, the compositions are administered orally, topically, intravenously, or in a combination thereof.

The oral pharmaceutical compositions useful in this invention may be in any orally acceptable dosage form including, but not limited to, capsules, tablets, aqueous suspensions or solutions. In the case of tablets for oral use, carriers which are commonly used include calcium carbonate, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The topical pharmaceutical composition useful in this invention may be formulated in a suitable ointment containing the active component suspended or dissolved in one or more carriers. Carriers for topical compositions include, but are not limited to, glycerine, mineral oil, liquid petrolatum, white petrolatum, ethanol, propanol, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, ethanol, propanol, benzyl alcohol and water.

The pharmaceutical compositions used in the methods of this invention may also be administered intravenously. A formulation suitable for intravenous administration comprises progesterone dissolved in an alcohol and mixed with a suitable carrier such as fat emulsions. The amount of progesterone in the alcohol solution can be varied from 1 g/Liter to a saturated solution of progesterone in alcohol. In a preferred embodiment, an ethanolic solution of progesterone is mixed with a fat emulsion and the resulting formulation is administered intravenously. The ratio of the ethanolic progesterone solution and the fat emulsion can range from 1:5 v/v to 1:15 v/v. Preferably, the ratio of the ethanolic progesterone solution and the fat emulsion is 1:10 v/v.

Any device useful for intravenous (I.V.) administration may be used to deliver the I.V. progesterone compositions for use in the methods of the present invention. These devices include peripherally inserted catheters, tunneled catheters, multi or triple lumen catheters, implanted ports, epidural or subcutaneous infusion techniques.

In a preferred embodiment, a peripherally inserted catheter, typically inserted into the forearm, is used for intravenous administration.

In another preferred embodiment, a tunneled catheter, such as Hicman Catheter, is used for intravenous administration.

According to the methods of the present invention, one or more of the above routes of administering the progesterone composition may be used in treating the undesirable side effects. In a preferred embodiment, a pharmaceutical composition comprising natural progesterone is administered intravenously in an amount effective to deliver 6–9 g/day of progesterone for at least one day or until the undesirable side effects are substantially mitigated. This is followed by oral or topical administration, or a combination thereof, of a pharmaceutical composition in an amount effective to deliver at least 1 g/day of natural progesterone. The treatment is continued as long as the side effects persist.

A second aspect of the invention provides high dosage pharmaceutical compositions of progesterone useful in treating the undesirable side effects of progestins or progesterone analogues used for birth control. These compositions comprise an amount of natural progesterone effective in alleviating the effects of said progestins or progesterone analogues and a pharmaceutically acceptable carrier.

The amount of progesterone present in the composition can vary from 1% to 99.99% by weight. Preferably, progesterone is present at 10% to 90% by weight. More preferably, progesterone is present at 30% to 70% by weight.

The second component of the pharmaceutical compositions of this invention is a pharmaceutically acceptable carrier. Pharmaceutically acceptable carriers that may be used in these pharmaceutical formulations include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, $C_{1-6}$ alcohols, polyethylene glycol, sodium carboxymethylcellulose, polyacrylates, waxes, polyethylene-polyoxypropylene-block polymers, polyethylene glycol and wool fat.

In a preferred embodiment, the formulation is suitable for oral administration. In a preferred oral formulation, the pharmaceutically acceptable carrier is calcium carbonate. The ratio of progesterone to calcium carbonate in these formulations ranges from 1:1 by weight to 10,000:1 by weight.

In a more preferred oral formulation, the ratio of progesterone to calcium carbonate ranges from 2:1 by weight to 4:1 by weight and is administered in a capsule of suitable size.

In the most preferred oral formulation, the ratio of progesterone to calcium carbonate in the capsule is 4:1 by weight, wherein 200 mg of natural progesterone is present in each capsule.

In another preferred embodiment, the formulation is suitable for topical administration. In a preferred topical formulation, a solution of progesterone is prepared in alcohols and water wherein the amount of progesterone in the solution varies from 0.1% to 25% by weight. In a more preferred topical formulation, progesterone is dissolved in a mixture of glycerin, ethanol and water wherein the amount of progesterone in the solution varies from 0.1% to 25% by weight.

In another preferred topical formulation, progesterone is mixed into a suitable cream base and propylene glycol to give a cream containing progesterone in an amount varying from 0.1% to 25%.

In order that the invention described herein may be more fully understood, the following examples are set forth. It should be understood that these examples are for illustrative purposes only and are not to be construed as limiting this invention in any manner.

EXAMPLE 1

Topical Progesterone Cream

Micronized Progesterone U.S.P. (10 g) was placed in a mortar and smoothed to a paste using a minimum amount of propylene glycol. The resulting paste was placed in an electric mixer and Unibase™ cream or Vanicream™ (40 g) was added to the paste. The mixture was then blended to yield a cream suitable for topical application having approximately 20% progesterone by weight.

2.5 ml of 20% progesterone cream was applied topically each day on the patient's chest and inner thighs until the patient experienced relief from the undesirable side effects.

EXAMPLE 2

Topical Progesterone Solution

Progesterone Wettable U.S.P. (5 g) was dissolved in a minimum amount of 95% ethanol. Glycerin (40 g) was added to the resulting solution and stirred to give a homogeneous solution suitable for topical application and containing approximately 10% progesterone by weight.

2.5 ml of 10% progesterone cream was applied topically each day on the patient's chest and inner thighs until the patient experienced relief from the undesirable side effects.

EXAMPLE 3

Oral Progesterone Capsules

Micronized Progesterone U.S.P. (5 g) and calcium carbonate U.S.P. (20 g) were placed in a grinding mill and blended to yield a homogenous powder. The resulting powder was then placed in a gelatin capsule suitable for oral administration and containing 200 mg of progesterone by weight.

3 capsules, each containing 200 mg of progesterone by weight, was administered five times a day. This treatment was continued daily until the patient experienced total relief from the undesirable side effects.

EXAMPLE 4

I.V. Progesterone Solution

Progesterone (Wettable) U.S.P. (4 g) was dissolved in 50 ml of ethanol and placed in a 120 ml Glass Amber BHI. The mixture was warmed slightly to facilitate the dissolution of progesterone.

50 ml of this solution was drawn into a 60 ml syringe bearing an 18 gauge needle. The needle was replaced with a 2 millimicron filter, and a new 18 gauge needle was attached to the filter. The solution was then syringed into 500 ml of Liposyn III™ (20%). The resulting formulation was used within 24 hours for intravenous administration.

The above formulation was administered intravenously through a Hicman catheter in an amount which effectively delivered 6.6 g of progesterone daily for six days. The patient reported a substantial reduction in every undesirable side effect previously experienced. The swelling in the joints reduced significantly and the patient was able to walk without any pain.

EXAMPLE 5

Treatment Of A Female Suffering From The Side Effects Of Levonorgestrel Implants A twenty-nine year old female patient had five tubes containing levonorgestrel implanted subdermally in her arm. After approximately one month, she developed pain in her shoulder. After four more months the pain spread to various joints and muscles. After the sixth month she became highly irritable and suffered acute depression. She also started losing weight. Over the next four months these symptoms increased in severity, and were accompanied by headache and a general sense of illness. Approximately twelve months after the subdermal implantation, the tubes containing levonorgestrel were removed from her arm.

The symptoms, however, persisted and the patient continued to suffer from weight loss, acute fatigue, lack of appetite, severe depression and angry outbursts. The pain and swelling in the joints and muscles precluded movement without acute pain. The patient required assistance for walking and was essentially bedridden. This physical condition persisted for approximately twenty four months after the removal of the subdermal contraceptive.

The patient tested positive for PMS. Tests performed to ascertain an onset of arthritis yielded negative results.

The patient was administered a daily intravenous dose of 6.6 grams of natural progesterone dissolved in ethanol using a Hicman catheter for six consecutive days. At the end of six days the patient reported a substantial decrease in pain along with a significant reduction in the swelling of the joints. The Hicman catheter was removed after six days. After the catheter was removed, there was a slight recurrence of the side effects over the next two weeks.

The patient was then treated with an oral composition containing 200 mg of micronized progesterone and 50 mg of calcium carbonate. The patient received three capsules five times a day for a total dosage of 3 g of micronized progesterone each day. The patient reported a further reduction in her irritability, and an elimination of depression and all joint pains. She also regained her ability to walk without pain.

While we have hereinbefore presented a number of embodiments of this invention, it is apparent that the claimed invention can be altered to provide other embodiments which utilize the methods of this invention. Therefore, it will be appreciated that the scope of this invention is to be defined by the claimed appended hereto rather than the specific embodiments which have been presented hereinbefore by way of example.

I claim:

1. A method for treating the undesirable side effects of progestins or progesterone analogues administered for birth control in a human female, said method comprising the step of administering to said female a pharmaceutical composition comprising natural progesterone in an amount effective in alleviating said undesirable side effects and a pharmaceutically acceptable carrier.

2. The method according to claim 1, wherein said undesirable side effects are selected from headache, mood changes, nervousness, abdominal cramps, dizziness, weakness or fatigue, nausea, vaginal irritation, breast swelling and tenderness, bloating, swelling of the hands or feet, backache, depression, mastalgia, insomnia, acne rashes, hot flashes, angry outbursts, acute weight gain/loss, pain and swelling of the joints, hypertension, stroke, vomiting and combinations thereof.

3. The method according to claim 1, wherein the amount of natural progesterone administered to said female is between 200 mg/day to 20 gm/day.

4. The method according to claim 3, wherein the amount of natural progesterone administered to said female is between 2 gm/day to 10 gm/day.

5. The method according to claim 4, wherein the amount of natural progesterone administered to said female is between 6 gm/day to 9 gm/day.

6. The method according to any one of claims 1 to 5, wherein said progestin or progesterone analogue used for birth control is levonorgestrel.

7. The method according to any one of claims 1 to 5, wherein said progestin or progesterone analogue used for birth control is medroxyprogesterone acetate.

8. The method according to any one of claims 1 to 5, wherein said pharmaceutical composition is administered orally to the patient.

9. The method according to any one of claims 1 to 5, wherein said pharmaceutical composition is administered intravenously to the patient.

10. The method according to any one of claims 1 to 4, wherein said pharmaceutical composition is administered topically to the patient.

* * * * *